United States Patent
Tonsich

(10) Patent No.: US 10,287,940 B2
(45) Date of Patent: May 14, 2019

(54) MOVABLE EMISSION CONTROL SYSTEM FOR AUXILIARY DIESEL ENGINES

(71) Applicant: Clean Air-Engineering—Maritime, Inc., San Pedro, CA (US)

(72) Inventor: Nicholas G. Tonsich, San Pedro, CA (US)

(73) Assignee: Clean Air-Engineering—Maritime, Inc., San Pedro, CA (US)

( * ) Notice: Subject to any disclaimer, the term of this patent is extended or adjusted under 35 U.S.C. 154(b) by 0 days.

(21) Appl. No.: 15/619,197

(22) Filed: Jun. 9, 2017

(65) Prior Publication Data

US 2017/0342883 A1 Nov. 30, 2017

Related U.S. Application Data

(63) Continuation-in-part of application No. 15/231,071, filed on Aug. 8, 2016.
(Continued)

(51) Int. Cl.
*F01N 3/10* (2006.01)
*F01N 3/035* (2006.01)
(Continued)

(52) U.S. Cl.
CPC .............. *F01N 3/10* (2013.01); *B01D 53/62* (2013.01); *B01D 53/84* (2013.01); *B01D 53/92* (2013.01); *B63H 20/245* (2013.01); *C12M 43/04* (2013.01); *F01N 3/021* (2013.01); *F01N 3/035* (2013.01); *F01N 13/004* (2013.01);
(Continued)

(58) Field of Classification Search
CPC ........ F01N 3/10; F01N 3/035; F01N 2590/02; B01D 53/62; B01D 53/84; B01D 53/92; B01D 2257/504; B01D 2258/012; B63H 20/245; C12M 43/04
See application file for complete search history.

(56) References Cited

U.S. PATENT DOCUMENTS 6,022,389 A * 2/2000 Vross .................... B01D 46/00
126/343.5 A
6,989,045 B2 1/2006 Bailey et al.
(Continued)

FOREIGN PATENT DOCUMENTS

WO 2008092964 A1 8/2008

OTHER PUBLICATIONS

Exhaust Treatment/Clean Air Engineering—Maritime; Jul. 30, 2015; retrieved on Nov. 9, 2016; https://web.archive.org/web20150730144033/http://caemaritime.com/what-we-do/exhaust-treatment/; 2pp.

*Primary Examiner* — Patrick D Maines
(74) *Attorney, Agent, or Firm* — Avyno Law P.C.

(57) ABSTRACT

A mobile emissions control system is provided for diesel engines operated on ocean-going ships at-berth. The emissions control system comprises two essential elements: an emissions capturing system and an emissions control system. The emissions control system may be mounted on a towable chassis or mounted on a barge, allowing it to be placed alongside ocean-going ships at-berth. The emission capturing system captures exhaust from a ship's diesel engine and conducts it into the emissions control system, which cleans the exhaust and then passes clean air into the atmosphere through an exhaust outlet.

3 Claims, 14 Drawing Sheets

Related U.S. Application Data

(60) Provisional application No. 62/201,925, filed on Aug. 6, 2015, provisional application No. 62/401,753, filed on Sep. 29, 2016.

(51) Int. Cl.
*B63H 20/24* (2006.01)
*C12M 1/00* (2006.01)
*B01D 53/84* (2006.01)
*B01D 53/92* (2006.01)
*B01D 53/62* (2006.01)
*F01N 13/00* (2010.01)
*F01N 3/021* (2006.01)

(52) U.S. Cl.
CPC .. *B01D 2257/504* (2013.01); *B01D 2258/012* (2013.01); *F01N 2340/00* (2013.01); *F01N 2590/02* (2013.01); *F01N 2610/02* (2013.01); *Y02T 10/20* (2013.01)

(56) References Cited

U.S. PATENT DOCUMENTS

| | | | |
|---|---|---|---|
| 8,075,651 B2 | 12/2011 | Caro et al. | |
| 9,089,806 B2 | 7/2015 | Powell et al. | |
| 2003/0110763 A1* | 6/2003 | Pawson | B01D 53/9431 60/286 |
| 2004/0020364 A1* | 2/2004 | Koclejda | B01D 46/002 95/273 |
| 2005/0244318 A1* | 11/2005 | Caro | B01D 53/92 423/212 |
| 2007/0209544 A1* | 9/2007 | Caro | B61C 5/02 105/26.05 |
| 2010/0180559 A1* | 7/2010 | Caro | B08B 15/02 55/385.1 |
| 2011/0265449 A1* | 11/2011 | Powell | B63H 21/32 60/272 |
| 2012/0102929 A1 | 5/2012 | Beissler et al. | |
| 2014/0090379 A1* | 4/2014 | Powell | B63H 21/32 60/686 |
| 2017/0342883 A1* | 11/2017 | Tonsich | F01N 3/10 |

\* cited by examiner

MOVABLE EMISSION CONTROL SYSTEM FOR AUXILIARY DIESEL ENGINES

RELATED APPLICATIONS

This is a continuation-in-part application and claims priority of U.S. Application Ser. No. 62/401,753, filed on Sep. 29, 2016, titled MOVABLE EMISSION CONTROL SYSTEM FOR AUXILIARY DIESEL ENGINES; and U.S. patent application Ser. No. 15/231,071, filed on Aug. 8, 2016, titled EMISSION CONTROL SYSTEM FOR AUXILIARY DIESEL ENGINES; both application of which are incorporated in their entirety by reference in this application.

FIELD OF THE INVENTION

The invention relates to a movable emissions reduction system, and in particular, a movable airborne toxic emissions reduction system for auxiliary diesel engines operated on ocean-going ships (or vessels) at-berth.

BACKGROUND OF THE INVENTION

The California Air Resources Board ("CARB") has adopted a regulation commonly called the at-berth regulation, the purpose of which is to reduce emissions from diesel auxiliary engines on container ships, passenger ships and refrigerated-cargo ships while berthing at a California Port, which the regulation defines as the Ports of Los Angeles, Long Beach, Oakland, San Francisco and Hueneme. Other jurisdictions have or are considering adopting similar regulations. The at-berth regulation provides vessel fleet operators visiting regulated ports two options to reduce at-berth emissions from auxiliary engines: (1) turn off auxiliary engines and connect the vessel to some other source of power, most likely grid-based shore power; or (2) use alternative control technique(s) that achieve equivalent emission reductions.

Current options for connecting to alternative power sources are often cumbersome and expensive, and are sometimes not available for a number of reasons, including one or more of the following reasons: (i) ships are not wired for shore power; (ii) shipping companies do not want the expense of converting to shore power; (iii) terminals have no shore power available; or (iv) shore power is over-stressed and is unable to provide for additional demand.

Currently, few or no alternative control techniques are available that achieve equivalent emission reductions. Thus, a need exists for affordable alternatives to shore power connections. Absent such an economical solution, some vessels will be unable to dock at major ports (such as those in California), thus adversely affecting shippers' businesses. In addition, ports subject to the CARB at-berth regulation and/or regulations, or other similar restrictions, will also be adversely affected: not only will they lose business from ships that do not or cannot comply with applicable restrictions or regulations, but also they will be hindered in expanding business by attracting ships to dock that are similarly non-compliant.

SUMMARY

A movable emissions reduction system is provided that allows a ship at-berth to operate its auxiliary diesel engine or its engines with reduced emissions. As such, the emissions reduction system allows for compliance with applicable regulations and/or restrictions on emissions, such as the CARB regulation, or other similar restrictions or regulations. The present invention provides an efficient, economical and regulatory-compliant alternative to shore power (i.e. an Alternative Maritime Power Equivalent) at-berths for ocean-going ships that cannot or choose not to use shore power. Moreover, the invention is useful even where a ship is not regulated for shore power, but would like to operate with minimal environmental impacts. The invention ties directly to the stack of a ship's auxiliary diesel engine, and comprises two essential elements: an emissions capturing system and an emissions control system.

In one example of the invention, diesel engine exhaust is captured an emissions capturing system, which attaches to the stack of a ship's auxiliary diesel engine at one end and to the emissions control system at the other end. The emissions capturing system comprises a telescoping duct that can be manipulated by a telescoping crane. Optionally, the duct can be articulating duct that can be manipulated by an articulating crane.

The crane can either be located on a truck or a stand-alone mobile unit so that it is mobile, or alternatively may be mounted on a stationary tower. The exhaust captured by the emission capturing system is then fed to an emissions control system capable of controlling emissions. The emission control system is positioned within a housing that is mounted on a chassis, permitting the chassis to be moved alongside a ship at-berth by a vehicle (such as a tractor), so as to permit installation and removal. The emissions control system has an exhaust inlet for receiving diesel engine exhaust and an exhaust outlet for the clean air. Alternatively, the emissions reduction system may be mounted on a barge that is floated alongside a ship, rather than on a vehicle on shore.

A method is further provided that allows for ships at-berth to use alternative control technique(s) that achieve equivalent emission reductions. The method comprises the steps of incorporating an emissions control system on a movable chassis or barge that can be towed or floated alongside a ship at-berth and connected to the diesel engine exhaust outlet. An exhaust capturing system may then be attached to a vessels exhaust to capture the vessel's diesel exhaust. The capturing system then provides the exhaust to the emission control system for treating the exhaust and emitting regulatory compliant air from an exhaust outlet located on the emissions control system.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

DESCRIPTION OF FIGURES

The invention may be better understood by referring to the following figures. The components in the figures are not necessarily to scale, emphasis instead being placed upon illustrating the principles of the invention.

DETAILED DESCRIPTION

Figure 1:
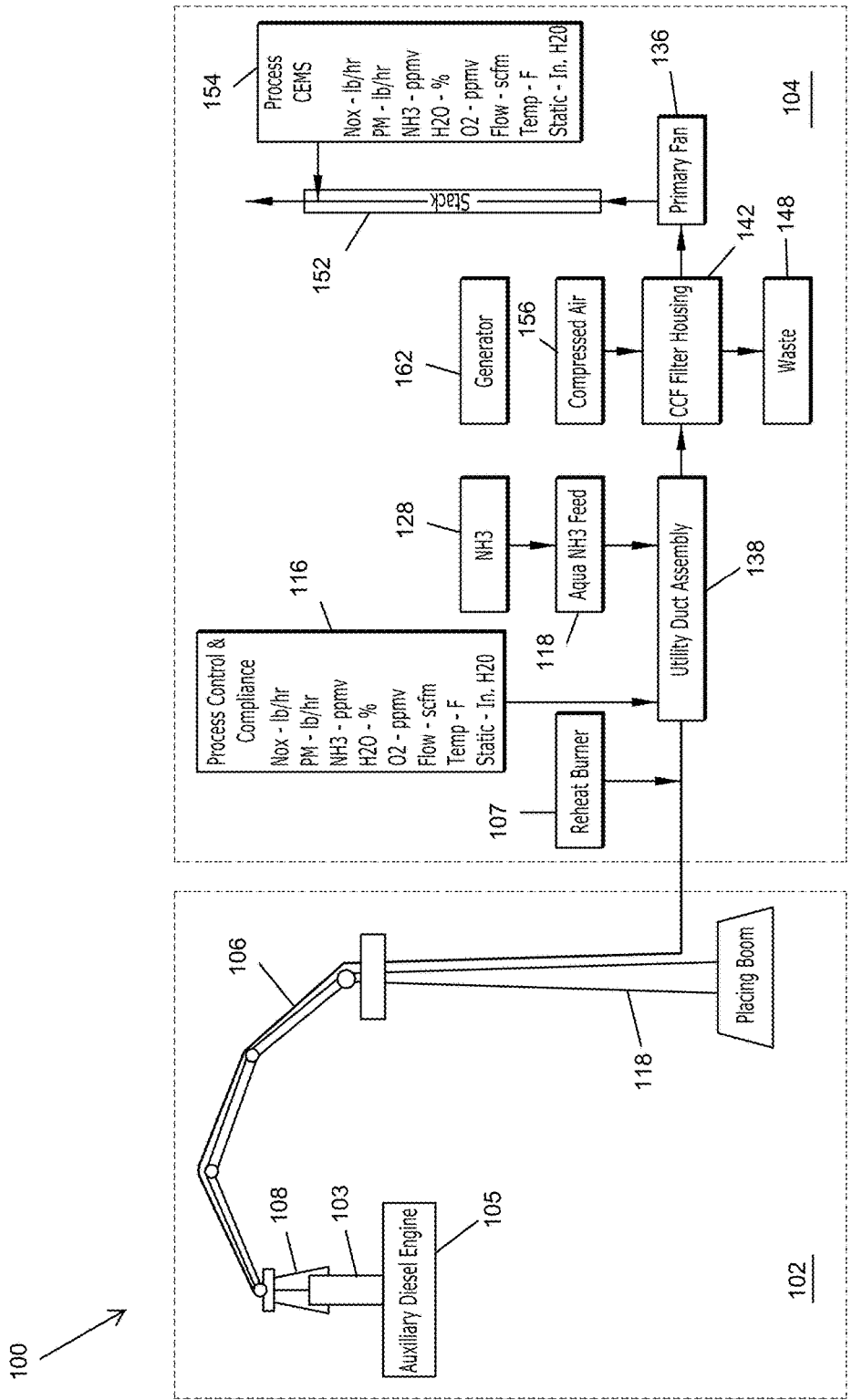
FIG. 1 is flow diagram of the emission reduction system of the present invention.
Figure 2:
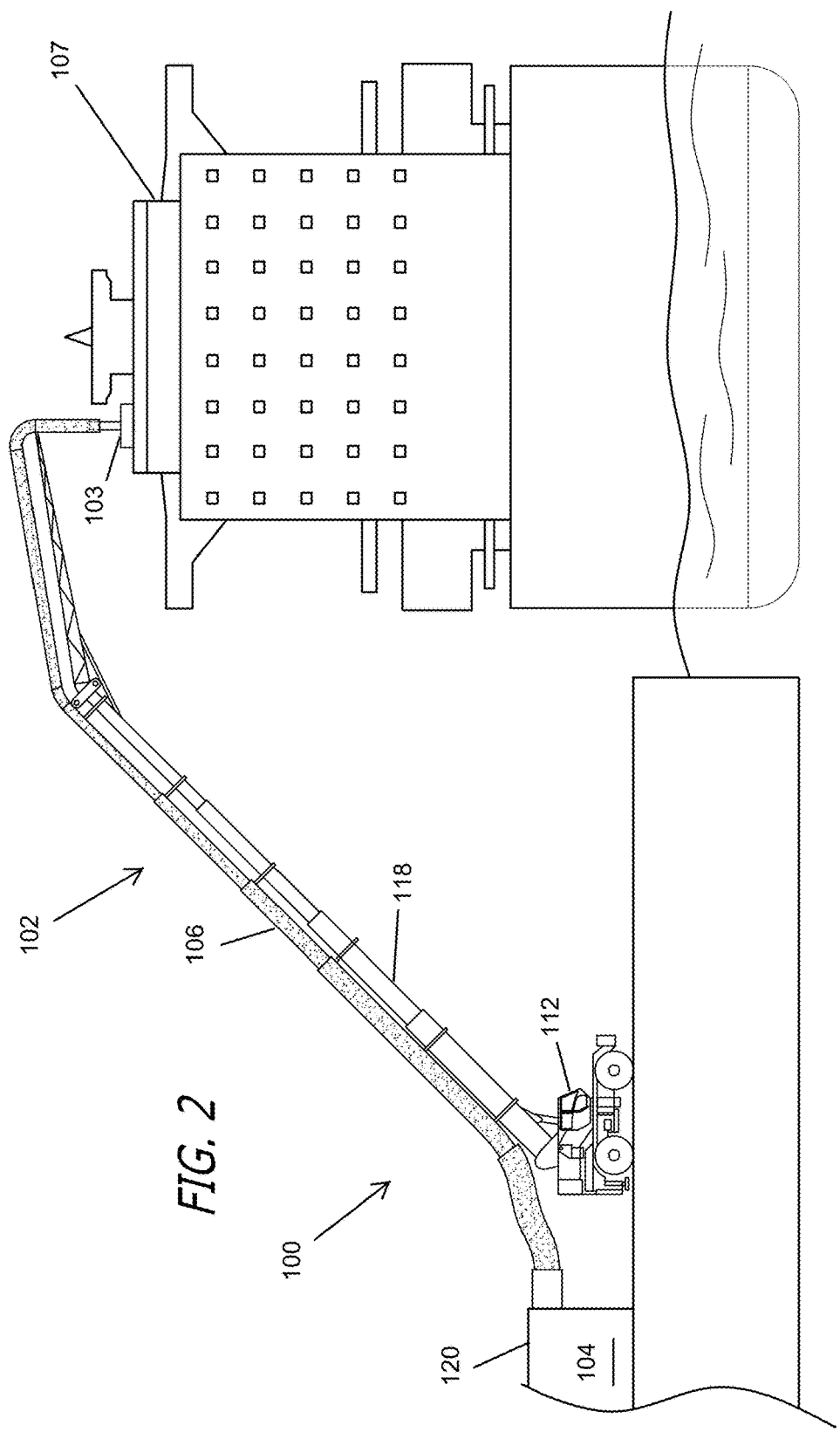
FIG. 2 is an elevation view of one example of an implementation of an emissions reduction system of the present invention where the emission control system is mounted to a mobile trailer and the emission capture system is a telescopic crane.

As illustrated by FIGS. 1-10, the present invention relates to an emissions reduction system 100 that is capable of reducing emissions from engines to allow for compliance with applicable regulations governing emissions, such as the requirements of the CARB regulation. As shown in FIGS. 1 and 2, the emissions reduction system 100 comprises both an emissions capturing system 102 and an emission control system 104.

As illustrated by FIG. 1, the emission capture system 102 extends a utility duct 106 over the ship's exhaust stack 103 to capture the exhaust from the auxiliary diesel engine 105. The duct 106 includes a connector and/or stack adapter 108 that connects the utility duck 106 to the exhaust. The duct 106 is extended over the ship's exhaust stack 103 using a crane or boom 118 that can be mobile or fixed. Those skilled in the art will recognize that any capturing system may be used that is capable of capturing a sufficient quantity of emissions so that the exhaust, once treated by the emissions control system 104, is regulatory compliant, without departing from the scope of the invention.

The emissions control system 104 receives the exhaust from the ship's auxiliary diesel engine 105 for processing from the duct 106. The emission control system 104 may be substantially contained within a housing 120 (See FIG. 2) and may move through the system via a utility duct assembly 138.

As shown in FIG. 1, a reheat burner 107 may be used to reheat the exhaust. Sensors 116 may also be positioned near the intake of the exhaust to monitor levels of particulate matter (PM), oxides of nitrogen ($NO_x$), carbon dioxide ($CO_2$), ammonia ($NH_3$), water content and oxygen ($O_2$), temperature and air flow prior. The sensors 116 may be located on a portion of the duct 106 either before or after entry into the housing 120. An aqueous ammonia injection port or feed 118 may also be included for treating the exhaust as further described below. The aqueous ammonia may be supplied via a storage tank 128.

The exhaust may then be filtered in a filter housing 142, using compressed air 156 to periodically clean the filters. The system 104 may be powered by a generator 162. Waste is collected 148 and the processed exhaust is then emitted through the emission control system exhaust stack 152. A fan 136 may be used to pull the exhaust through the utility duck assembly and out the control system exhaust stack 152. The system may further include monitors 154 for monitoring levels of particulate matter (PM), oxides of nitrogen ($NO_x$), carbon dioxide ($CO_2$), ammonia ($NH_3$), water content and oxygen ($O_2$), temperature and air flow prior of the exhaust after treatment.

One example of an implementation of the emission control system 100 of the present invention can be illustrated in FIG. 2. FIG. 2 is an elevation view of one example of an implementation of an emissions reduction system 100 of the present invention where the emission capture system 102 is mounted to a telescopic boom/crane 118 (as described further in connection with FIGS. 3-5). In this example, the emission capture system 102 includes a telescopic duct 106 sized to match the telescopic parts on the telescopic crane 112, such that the duct 106 can expand and retract with the movement of the telescopic part of the crane 112 (as further described in connection with FIGS. 3-4 below). By way of example, the telescopic crane 112 may be mounted on a truck or can be telescopic crawler crane (as shown) or a tracked telescopic crane.

It is recognized that, in addition to mounting a telescopic duct to a telescopic crane, the duct 106 may be mounted on or affixed to any type crane that can maneuver the duct 106. Alternatively, but not shown, the duct 106 may be articulated and may be mounted to an articulated crane, or may be mounted directly to a stationary or movable tower having a crane mounted thereon. The duct 106 may also be made of flexible material able to expand and reduce in size, or may include bends to match the articulation points in an articulated crane. The emissions capturing system 102 may also be mounted to a truck so as to make it movable, whereby the truck includes a crane 112.

The emissions capturing system 102 includes duct 106 of a length that can extend between the exhaust stack 103 of the ship 107 and the emission control system 104. The duct 106 includes a connection 108 (FIG. 1) or stack adapter that connects at one end to the stack 103 of a ship's auxiliary diesel engine 105 and at the other end to the emissions control system 104.

As illustrated by FIGS. 1-5, the duct 106 may be a telescopic duct 106 having ducts of differing diameter to allow the various piece to fit within one another in a telescoping manner. The duct 106 may otherwise be wholly or partially be flexible. As set forth above, the duct 106 may be rigid at one end (the end that connects to the emissions control system 104). At the other end, the duct connects to the ship's diesel exhaust through the connection device 108.

Figure 3:
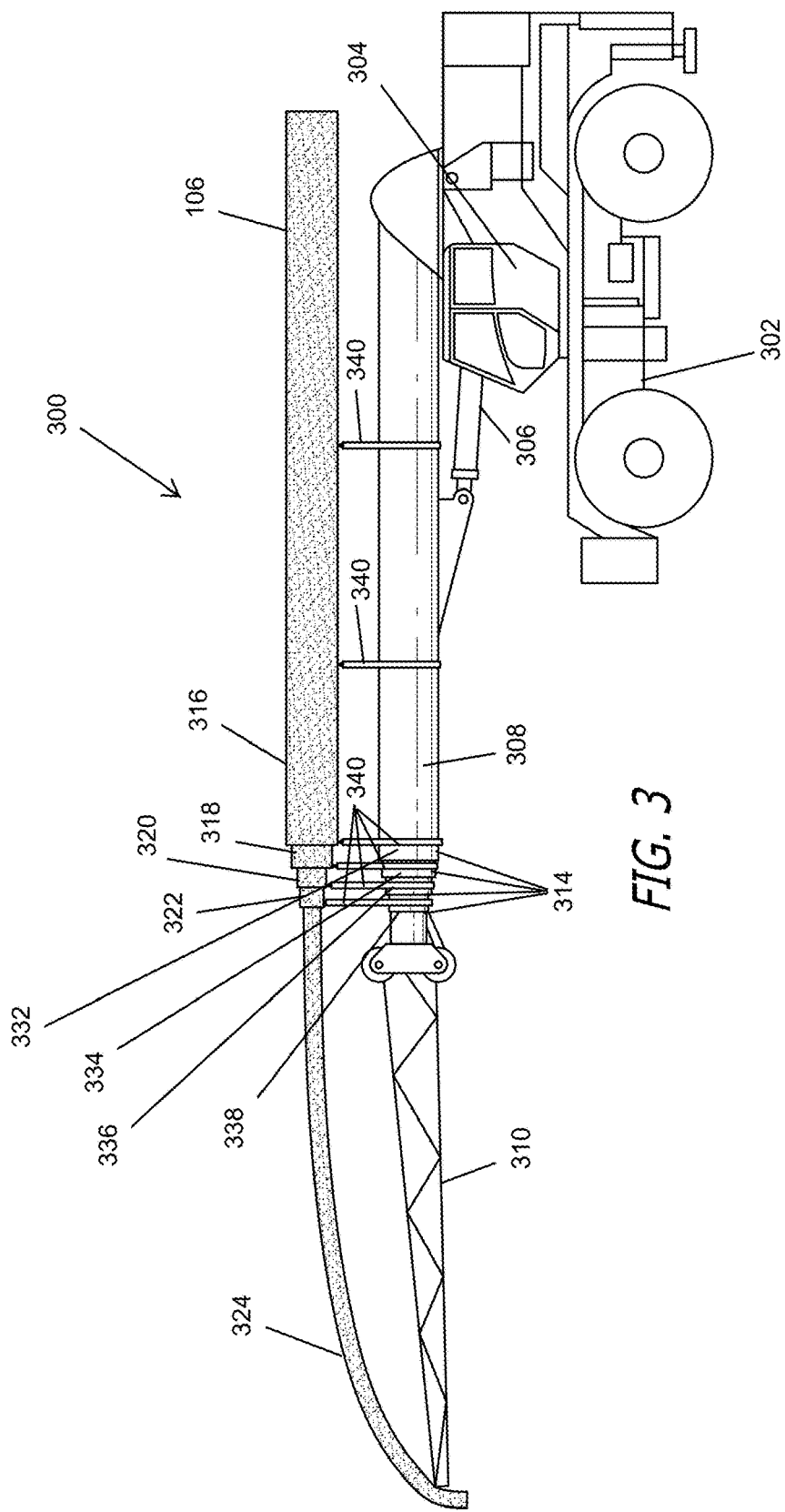
FIG. 3 is a side elevation view of one example of an implementation of the emissions capturing system comprised by the present invention.
Figure 4:
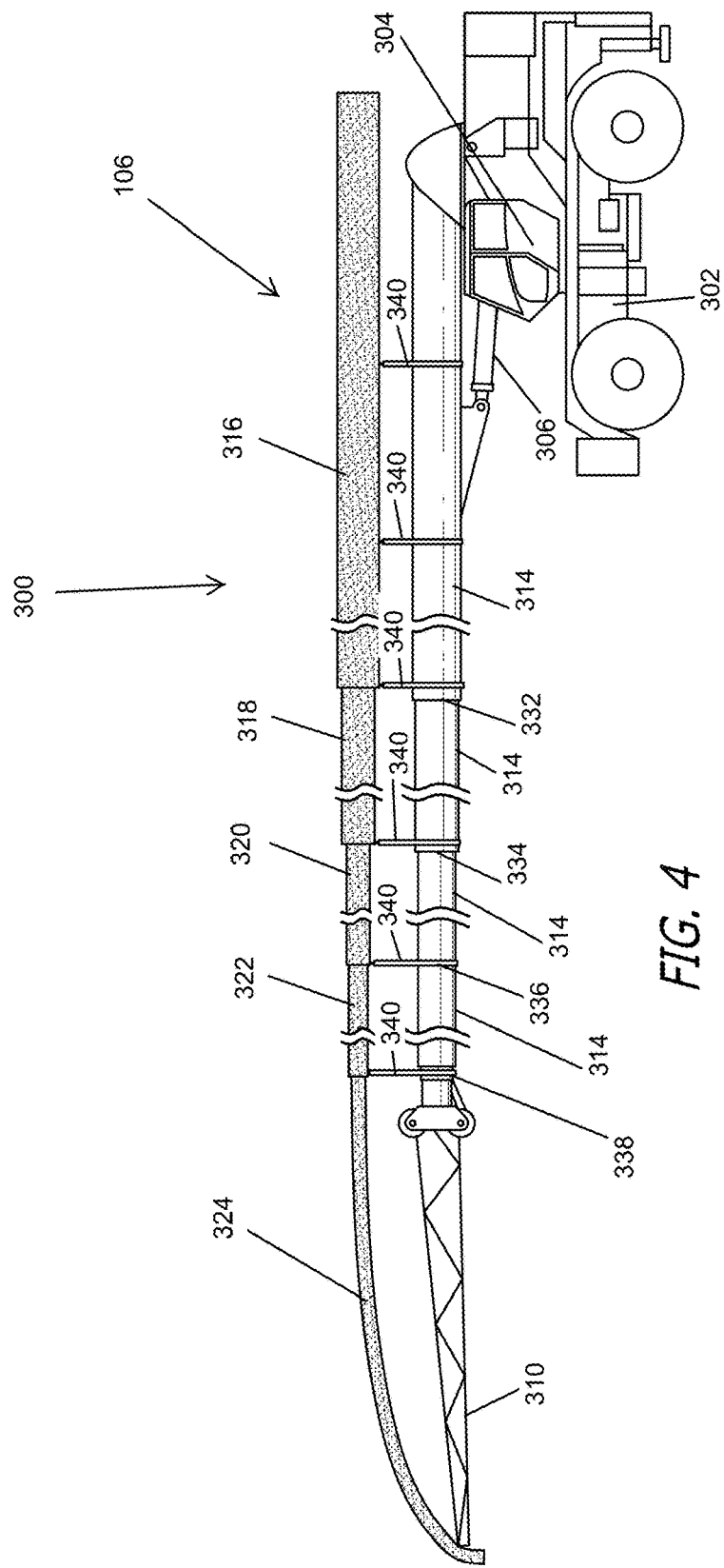
FIG. 4 is an elevation view of one example of an implementation of the emissions capturing system illustrating the crane and emissions control system extended.
Figure 5:
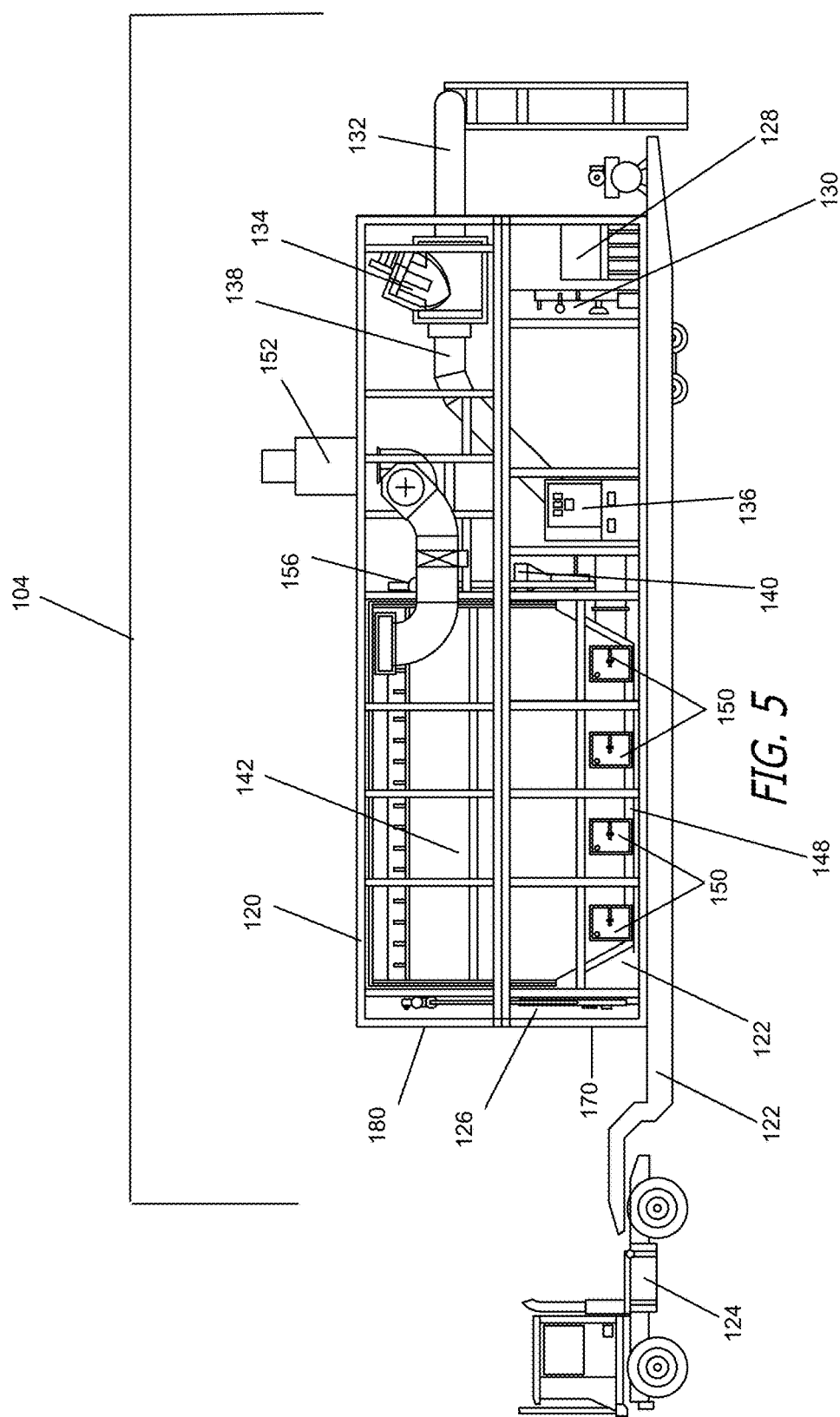
FIG. 5 is an elevation view of one example of the emissions control system of the present invention with the housing removed, mounted on a chassis attached to a tractor.

FIGS. 3-5 illustrate an example of telescopic duct 106 mounted on a telescopic crawler crane 300. In particular, FIG. 3 is a plan view of one example of an implementation of the emissions capturing system 102 comprised by the present invention. FIG. 4 is a side elevation view of one example of an implementation of the emissions capturing system 102 comprised by the present invention.

As illustrated in FIGS. 3 and 4, the crane 300 generally includes a chassis 302, an operating cabin 304, a luffing cylinder 306, a telescopic jib 308 and a hook block 310 or other extension accessory. The telescopic jib 308 includes multiple telescopic sections (e.g., first, second, third, fourth, to n number of sections) having ends that retract and extend into and out of the previous telescopic section 314.

The telescopic duct 106 also includes various telescopic sections that correspond in length and placement to the telescopic sections 314 of the jib 308. In the example, the jib 308 has first 316, second 318, third 320 and fourth 322 telescopic sections and the telescopic duct 106 also has corresponding first 332, second 334, third 336 and fourth 338 telescopic sections. The first telescopic section 332 of the duct 106 is mounted on the crane above the first section 316 of the telescopic jib 308 of the crane 300. The ends of each section 332, 334, 336, and 338 of the telescopic duct 106 are then also mounted to the ends of the corresponding sections of the telescoping jib 316, 318, 320 and 322, by, for example, connectors 340. In this manner, the telescopic sections of the duct 106 move with the telescopic sections of the jib 308 of the crane 300. This movement of the duct 106 with the crane is best illustrated in FIG. 5.

The duct 106 may also include a flexible end that may include an articulated bend or be able to bend to be mounted over the exhaust shaft 103 of the ship 107. An accessory 310 may be used on the end of the jib 308 to lower the duct 106 over the stack 103 as illustrated in FIG. 2.

As illustrated in FIG. 4, the telescopic sections of the duct 106 move with the telescopic sections of the jib 308 of the crane 300. The jib 308 has first 316, second 318, third 320 and fourth 322 telescopic sections and the telescopic duct 106 also has corresponding first 332, second 334, third 336 and fourth 338 telescopic sections. The ends of each section 332, 334, 336, and 338 of the telescopic duct 106 are then also mounted to the ends of the corresponding sections of the telescoping jib 316, 318, 320 and 322, by, for example, connectors 340, such that when the telescopic jib 308 expands, the telescopic duct 106 expands.

As illustrated in FIGS. 2-4, the hook block of the crane may be replace by another component that can accommodate additional ducting 106 and that can better assist with maneuvering the duct 106 over the ship's exhaust stack 103. The component or accessory can function as a fifth section 202 of the jib 308 that can support another section 204 of duct 106 having a connector or adapter 108 that may positioned on the end of the duct 106 to connect the duct 106 to the ship's exhaust stack 105. This section 204 of the duct 106 may include an articulating bend 206 to move the duct 106 downward over the ship's exhaust stack 105. In operation, the duct 106 is connected to the exhaust stack 105 of the diesel engine 107 and the diesel exhaust is drawn from the ship through the duct 106 and into the emissions control system 104.

FIGS. 5-8 illustrate on example of an emission control system 104 of the present invention. As illustrated by the Figures, the emissions control system 104 may be a hot gas filtration system for exhaust generated from the operation of the ship's auxiliary diesel engines while the ship is at-berth. This implementation of the invention is but one example of a system that reduces emissions and that may be used to meet regulatory requirements, such as the CARB requirements. Those skilled in the art will recognize that any emission control system may be placed within the housing 120 that is able to clean the exhaust to be regulatory compliant without departing from the scope of the invention.

FIG. 5 is an elevation of one example of the emissions control system 104 of the present invention with the housing 120 removed, mounted on a chassis 122 attached to a tractor 124. As shown in FIG. 5, the emission control system 104 may be contained within a housing 120, the walls of which have been removed for purposes of illustrating the individual components of the emissions control system 104. The emission control system 104 can be mounted on the chassis 122 that can be towed alongside a ship at-berth by a standard tractor vehicle 124. The housing 120 is sized to fit on a commercially-available chassis, trailer or barge 122. In this illustrated example, the housing 120 may have an equivalent footprint of approximately 8.5' by 52.5'. Those skilled in the art will recognize that other sized housings may be used; however, it is desirable for the housing 120 to fit on a commercially-available chassis or barge 122.

When a ship is at-berth, the emissions control system 104 is connected to the ship's diesel exhaust outlet 103 by one of the types of emissions capturing system 102 describe above, so that the ship's engine exhaust can be drawn through the emissions control system 104, treated, and emitted as clean air from the emissions control system exhaust outlet 152. The emissions reduction system 100, employing an emission control system 102 such as that described in more detail below, can remain in continuous operation while the ship's engines are running. The emissions reduction system 100 can be disconnected from the ship 107 prior to its leaving port.

The emission control system 104 takes diesel engine exhaust, subjects it to treatment and releases it as clean air that is regulatory compliant and/or that has reduced emission. In this example, the emissions control system 104 is configured on two levels within the housing 120: a lower level 170 and an upper level 180.

Figure 6:
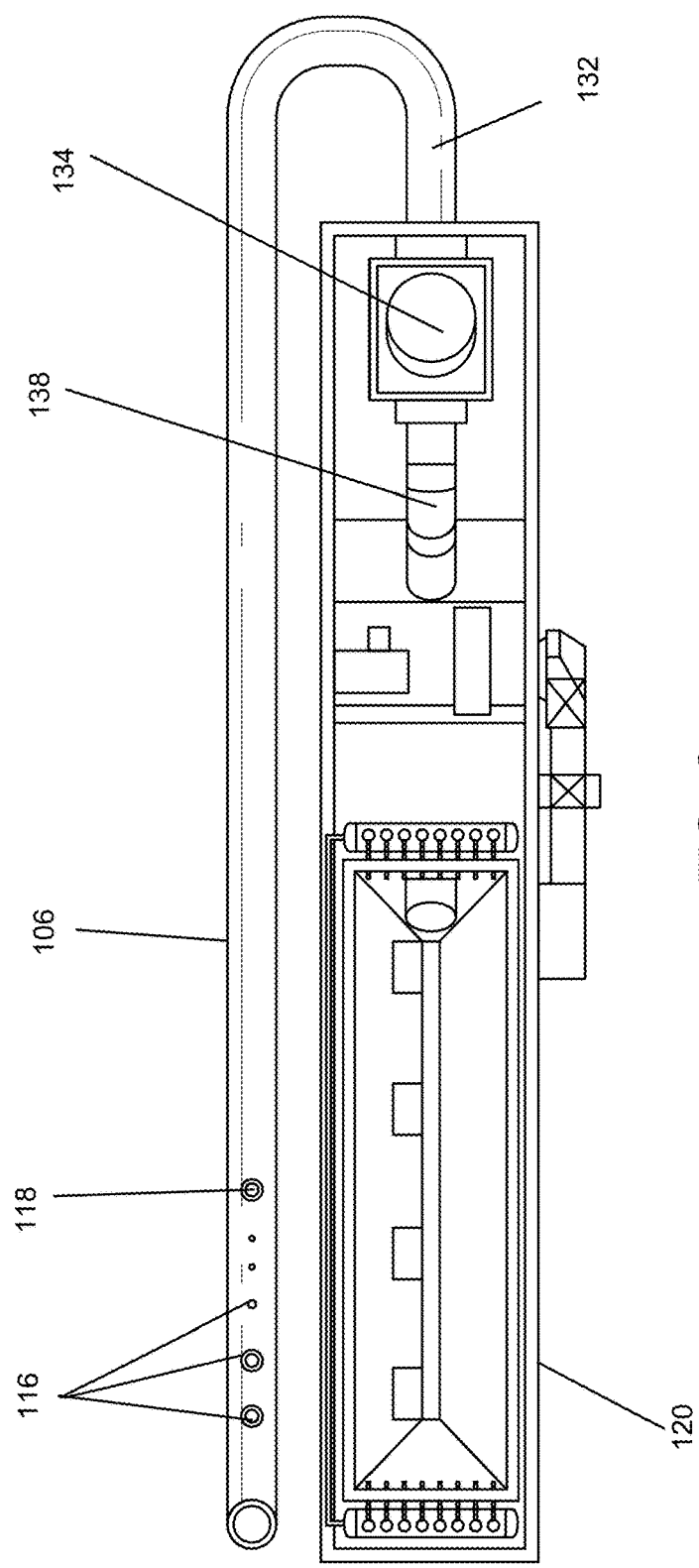
FIG. 6 is a plan schematic view of one example of the emissions control system of the invention with the housing removed.
Figure 7:
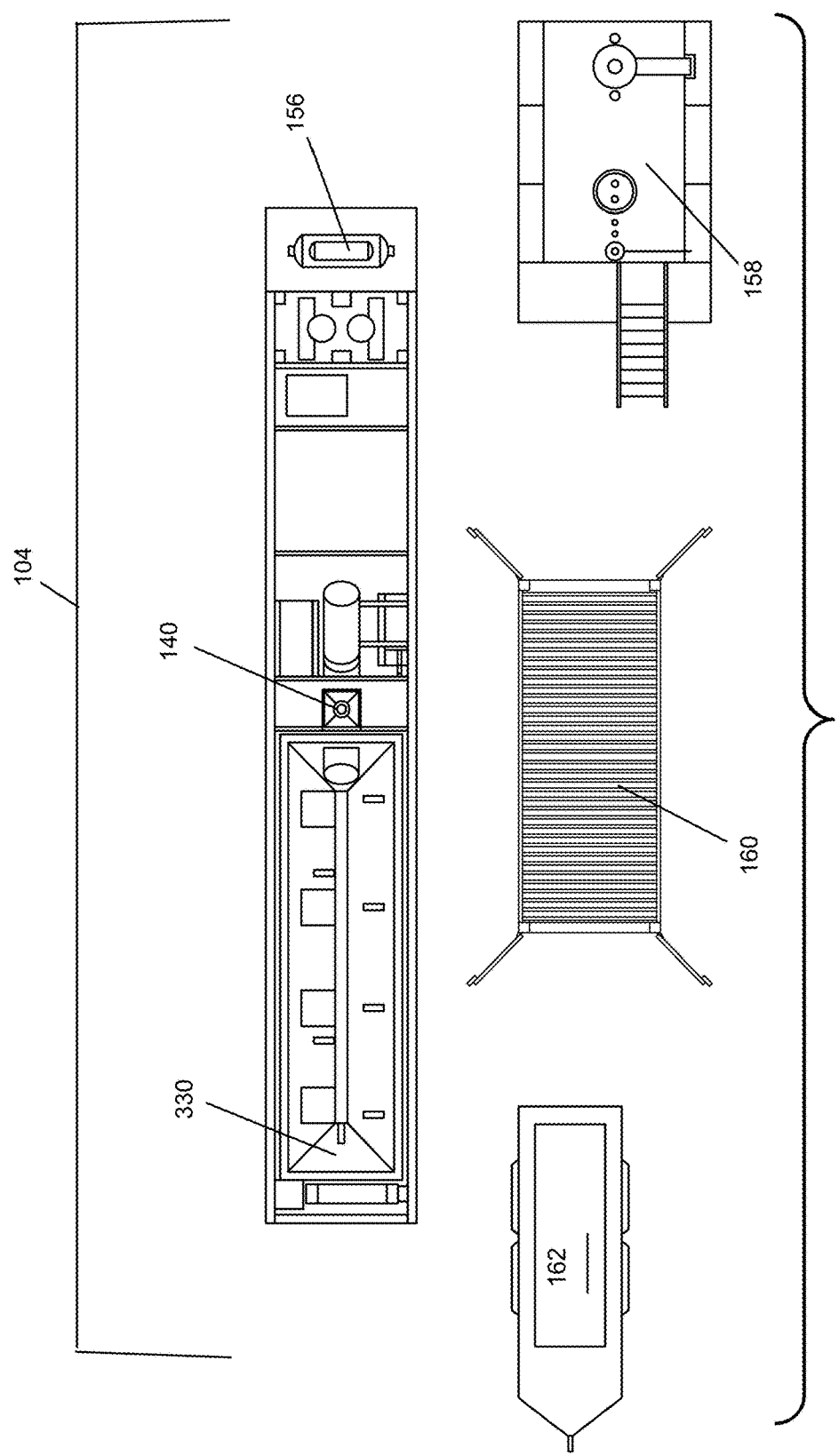
FIG. 7 is another plan schematic view of one example of the emissions control system of the invention, with the housing removed, mounted on a chassis attached to a tractor.
Figure 8:
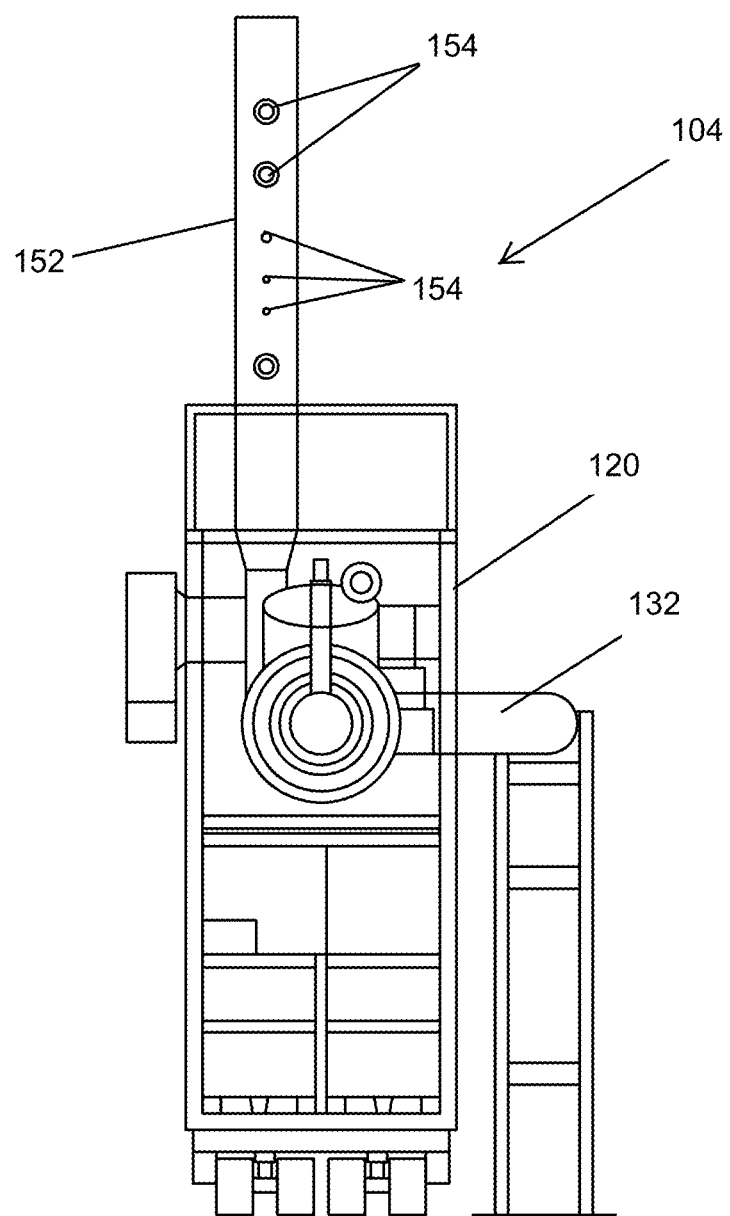
FIG. 8 is a rear elevation schematic view of one example of the emissions control system comprised by one example of an implementation of the invention, with the housing removed, mounted on a chassis.
Figure 10:
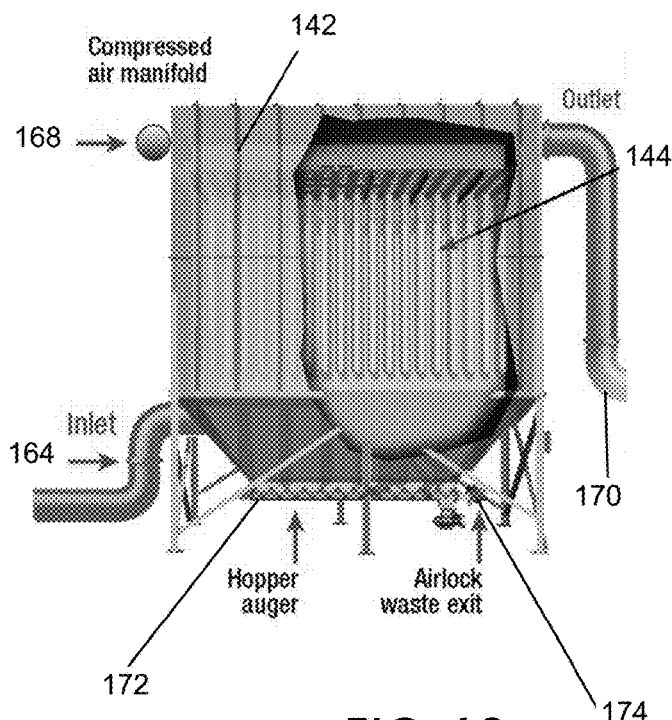
FIG. 10 illustrates an example of gas flow and particulate removal through the ceramic filter elements of FIG. 10.

In the illustrated example, the emission control system 104 is operated by a system control 126, and may be powered by a generator 162, shown in FIG. 7. The diesel exhaust is initially treated with aqueous ammonia (e.g. 19% aqueous ammonia) and dry sorbent. The aqueous ammonia may be injected into the exhaust stream before it is drawn into the emissions reduction system 104, although those skilled in the art would recognize that this injection may also occur after the exhaust enters the emissions reduction system 104 and before it enters the ceramic filter housing 142, as shown in FIG. 10. The aqueous ammonia may be stored within the housing 120 in a container 128 and pumped into the exhaust flow through an injection port 118, shown in FIG. 6, by a pump 130.

The exhaust is drawn into the emission control system 104 through an exhaust inlet duct 132. This may be by a fan 136 (FIG. 1). The exhaust first enters into a burner 134 powered by a burner gas train and control system 126, where it is heated to a temperature of between 350 to 950° F., in order to permit optimal treatment. A utility duct assembly 138 connects directly to the outlet of the burner 134, which connects to a ceramic filter housing 142. Before entering the ceramic filter housing 142, dry sorbent (e.g. sodium bicarbonate, trona or lime) is injected by a dry sorbent injector and feed 140.

Figure 9:
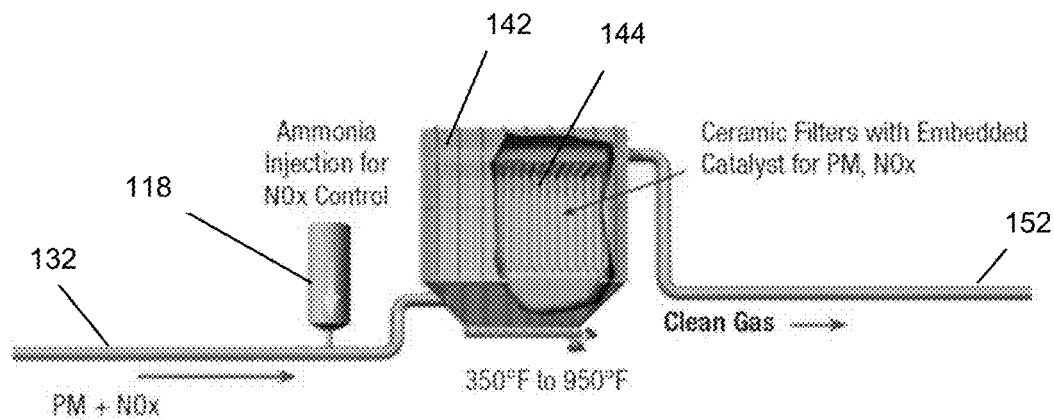
FIG. 9 illustrates an example of how ceramic filters arranged in a filter housing.
Figure 11:
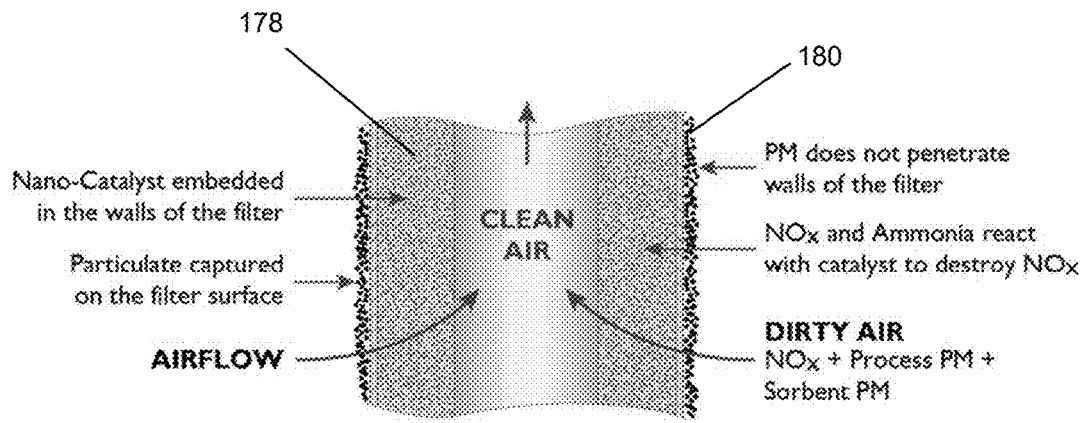
FIG. 11 is a cross-section of one example of a catalyst-embedded ceramic filter element.

After entering the ceramic filter housing 142 the exhaust is treated further by the ceramic filters 144, illustrated in FIGS. 9-11. Underneath the filter housing is a waste catch hopper 148 accessed by multiple access ports 150. The system 104 then emits the treated exhaust through an exhaust outlet stack 152 as clean air. This treated exhaust can be monitored for regulatory compliance by various monitors 154 located on the exhaust outlet stack 152, shown in FIG. 8. An access ladder (not shown) may be mounted within the housing 120, allowing access to all parts of the emission control system 100.

Other elements of the system may include an air compressor 156 for providing compressed air flow for the system, fuel tank 158, a control room 160 and a generator 162, as shown in FIG. 7.

As shown in FIG. 6, sensors 116 that monitor particulate matter (PM), oxides of nitrogen ($NO_x$), carbon dioxide ($CO_2$), temperature and air flow prior to the entry of the exhaust into the emissions control system 104 may be located on a portion of the duct 106, as well as an aqueous ammonia injection port 118 used for treating the exhaust as described below. Those skilled in the art will recognize that these sensors and the aqueous ammonia injection port could also be situated at other locations along the duct 106 or within the emissions control system 104 itself, e.g. on the utility duct assembly 138 located within the housing 120.

In operation, auxiliary engine exhaust is captured by the emissions capturing system 102, which is designed to capture the ship's auxiliary diesel engine exhaust and transport it to the emissions control system 104. An aqueous ammonia solution is drawn from the ammonia storage unit 128 by a pump 130, which is atomized and then sprayed into the exhaust, where it mixes with $NO_x$ in the exhaust stream. As noted above, this injection may occur prior to the entry of the exhaust stream into the emissions control system 104 or after it enters the system 104. After being injected with the aqueous ammonia spray, the exhaust is drawn directly into the emission control system 104 through the exhaust inlet 132. This may be done using a fan 136 (FIG. 1). The exhaust is first heated by the burner 134, where it is heated to the appropriate temperature. After leaving the burner 134, the exhaust travels through the utility duct assembly 138. While the exhaust is travelling through the utility duct assembly 138, dry sorbent is injected into the exhaust by a sorbent injector system 140. The dry sorbent may be stored in a dry sorbent storage container (not shown) located either within the housing 120 or outside of it. The dry sorbent reacts with $SO_2$, $SO_3$ and HCL to form solid particles that are captured by the ceramic filter elements 144. The exhaust stream then enters the ceramic filter housing 142 containing catalyst-embedded ceramic filter elements 144, where the added sorbent continuously deposits on the walls of the ceramic filter elements 144 and serves as the removal zone for PM. Restoring the low-pressure drop to the filter elements is accomplished by periodically sending a pulse of compressed air provided by the compressor 156 into the group of ceramic filter elements 144 while the system 104 is in operation. The operation causes the outer particle layer that deposits onto the ceramic filters to fall off into the waste catch 148, where it is removed and stored in a waste storage container (not shown).

The other gases, including NOx and ammonia ($NH_3$), penetrate the catalyst-embedded filter elements 144. On the catalyst surface, NOx is reacted with $NH_3$ and is reduced to diatomic nitrogen ($N_2$) and water vapor. The clean exhaust is then expelled into the atmosphere through the exhaust outlet stack 152.

FIG. 9 further illustrates the process by which the collected pollutant gas is treated by the emission control system 104. Pollutant gas passes into the system 104 through an exhaust inlet 132, where dry sorbent may be injected into the duct by the sorbent injector system 140, where it immediately starts to react with $SO_2$, $SO_3$ and HCl to form PM that will be captured by the ceramic filter elements 144 located in the ceramic filter housing 142. Aqueous ammonia is atomized and sprayed into the duct by the ammonia injector system 118, where it turns into a gas and mixes with NOx. This mixing is not affected by the process PM or the sorbent. The gas stream then passes into the ceramic filter housing 142, where the process PM and the sorbent are captured on the outside surface of the ceramic filter elements 144. The filters are periodically cleaned with a burst of compressed air from a compressed air blowdown 140 (FIGS. 1 and 5) while the filter housing 142 remains online. The NOx and ammonia mixture react on the large surface area of nano-catalysts embedded in the walls of the ceramic filter elements 144.

The mixture is free from PM that can blind or poison the catalyst, so the reaction can occur more efficiently and across a much wider temperature range. NOx are broken down into harmless $N_2$ and water vapor, which exit the system through the exhaust outlet stack 152.

FIG. 10 illustrates the ceramic filter elements 144 of one implementation of the invention 100, arranged in the ceramic filter housing 142, as well as the flow of treated exhaust gas through the ceramic filter housing 142. The exhaust gas, having been injected with dry sorbent and aqueous ammonia, enters the ceramic filter housing 142 at an inlet 164, where it is brought in contact with the ceramic filter elements 144, which are in the shape of elongated tubes arranged vertically within the ceramic filter housing 142. PM and sorbent are captured on the outside surface of these ceramic filter elements 144, which are periodically cleaned with a burst of compressed air from a compressed air blowdown (not shown) controlled by a compressed air manifold 168 while the filter housing remains online. The NOx and ammonia mixture react on the large surface area of nano-catalysts embedded in the walls of the ceramic filter elements 144. NOx are broken down into harmless $N_2$ and water vapor, which exit through the top of the ceramic filter housing 142 through an outlet 170. A hopper auger 172 collects the PM and sorbent blown down by the compressed air blowdown (not shown) that periodically cleans the ceramic filter elements 144, moving it into a waste exit 174.

FIG. 11 illustrates a cross-sectional view of one of the ceramic filter elements 144 and depicts the embedded catalyst 178. The ceramic filter element 144 captures most of the PM by inertial impaction, interception, Brownian diffusion and sieving on already collected particles that have formed a dust layer 180 on the ceramic filter element 144. The added sorbent continuously deposits on the walls of the ceramic filter element 144 and serves as the removal zone for the PM particles.

Figure 12:
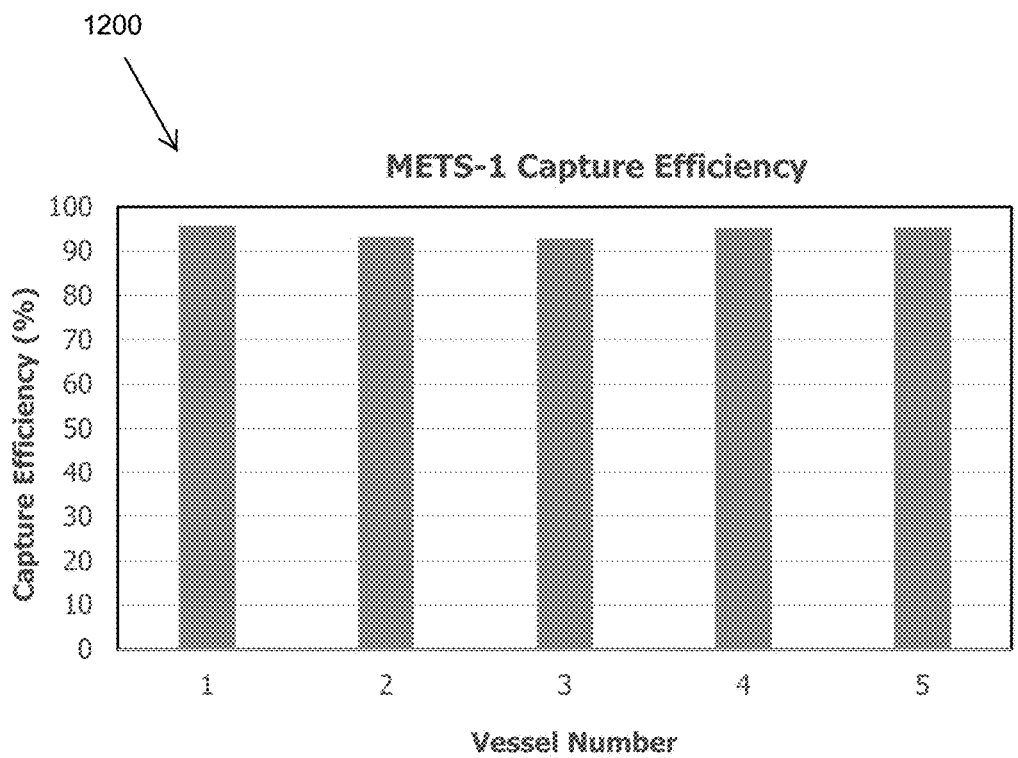
FIG. 12 is a chart illustrating the capture efficiency of one example of the invention.

FIG. 12 is a chart 1200 showing the emissions capture efficiency of various prototypes of the current invention from tests performed on five vessels for an average of 44 hours per vessel. The performance data illustrated in the chart shows a capture efficiency of more than 90% for each vessel and an average capture efficiency of 91.0% that has been certified by CARB for 90% capture efficiency.

Figure 13:
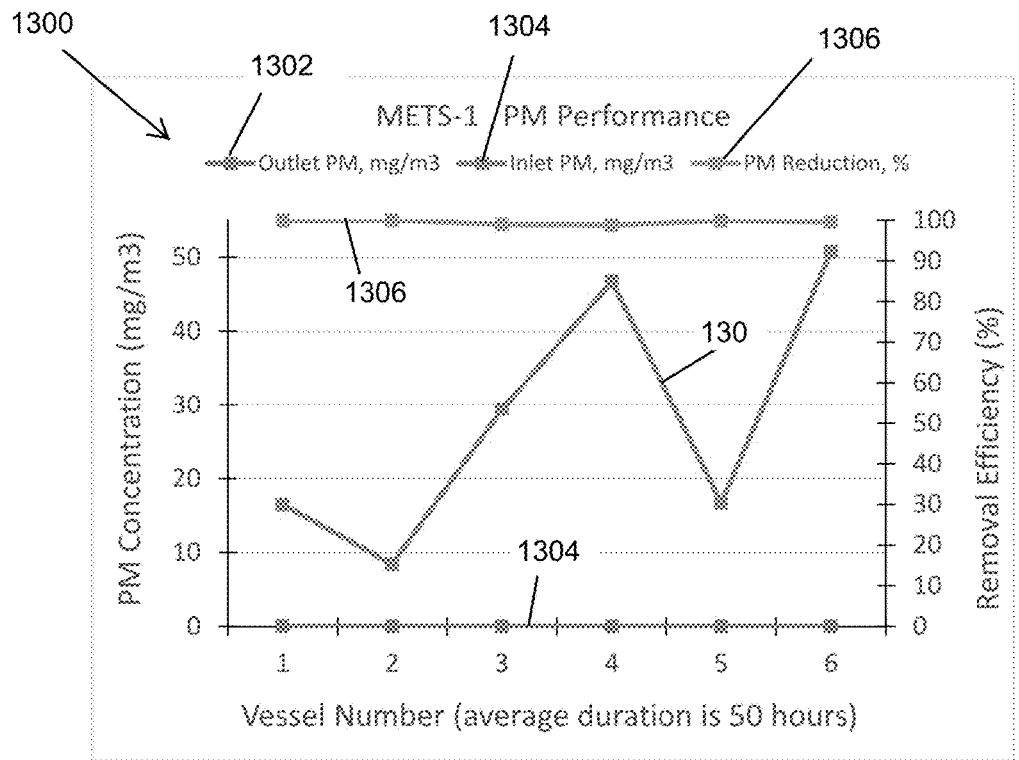
FIG. 13 is a chart illustrating particulate removal performance of one example of the invention.

FIG. 13 is a chart showing performance data for PM removal from tests performed on six vessels for an average of 50 hours per vessel. The chart shows an average PM removal of 99.5% that has been certified by CARB for 90% PM removal. Outlet PM (mg/m3) is shown by line 1302, inlet PM (mg/m3) is shown by line 1302 and PM reduction (mg/m3) is shown by FIG. 13.

Figure 14:
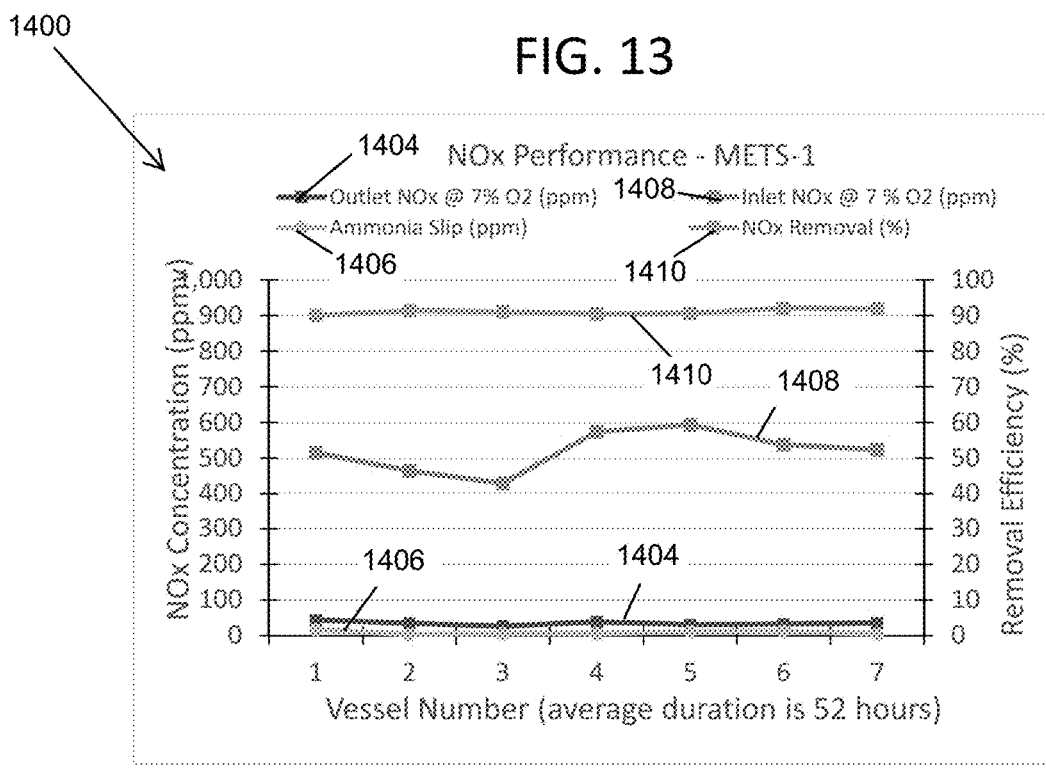
FIG. 14 is a chart illustrating oxides of nitrogen removal performance of one example of the invention.

FIG. 14 is a chart showing performance data for $NO_x$ removal from tests performed on seven vessels for an average of 52 hours per vessel. The chart shows an average $NO_x$ removal of 91.4% that has been certified by CARB for 90% capture efficiency. Outlet $NO_x$ (mg/m3) is shown by line 1402, ammonia slip (ppm) is shown by line 1406, inlet $NO_x$ (mg/m3) is shown by line 1408 and $NO_x$ removal (mg/m3) is shown by line 1410 is FIG. 14.

While the above example illustrates the emission control system 100 of the present invention mounted on a chassis 112 towed by a tractor 124, the emission control system may be positioned directly on land or the dock or may be mounted on a barge that may be towed alongside a vessel at-berth.

Without limiting the scope of the invention, the emission control system 104 may be paired with any of several extant technologies to facilitate reduction of $CO_2$ from the exhaust gas stream to regulatory-compliant levels. For example, a low temperature plasma method may be used, as illustrated by FIG. 15, or a $CO_2$ to algae process may be used in the emission control system, as illustrated by FIGS. 16 and 17.

Figure 15:
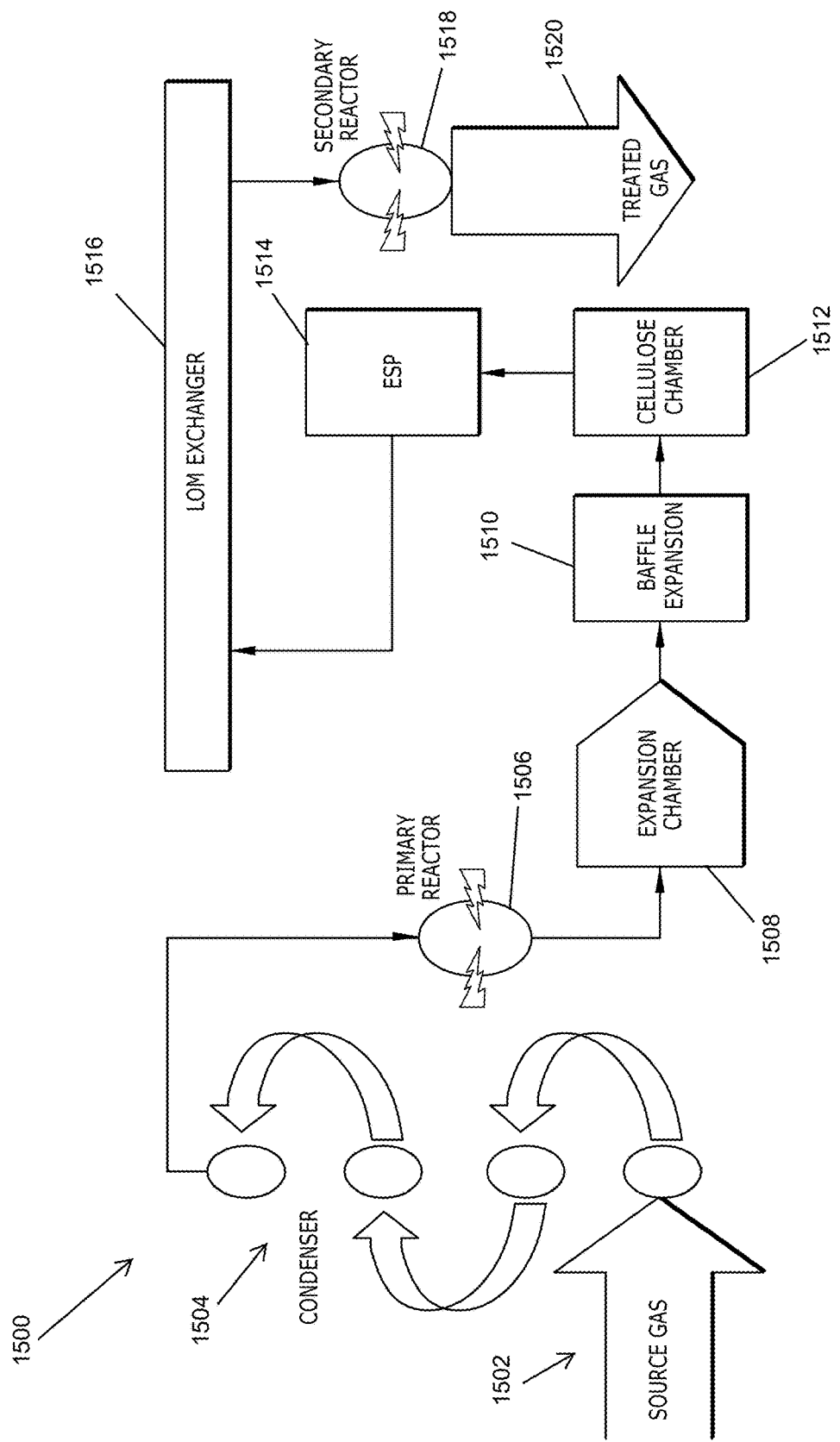
FIG. 15 is a chart illustrating carbon dioxide reduction in emissions using low temperature plasma.

FIG. 15 is a chart 1500 illustrating carbon dioxide reduction in emissions using low temperature plasma. In the example shown in FIG. 15, the source gas 1502 runs through a condenser 1504, then a primary reactor 1506. From the primary reactor 1506, the gas is passed to expansion chamber 1508, baffle expansion 1510 and cellulose chamber 1512 and then to the ESP 1514. From there, the gas 1516 is passed to the LOM exchanger 1516 and then to a second reactor 1518, resulting in treated gas 1520.

Figure 16:
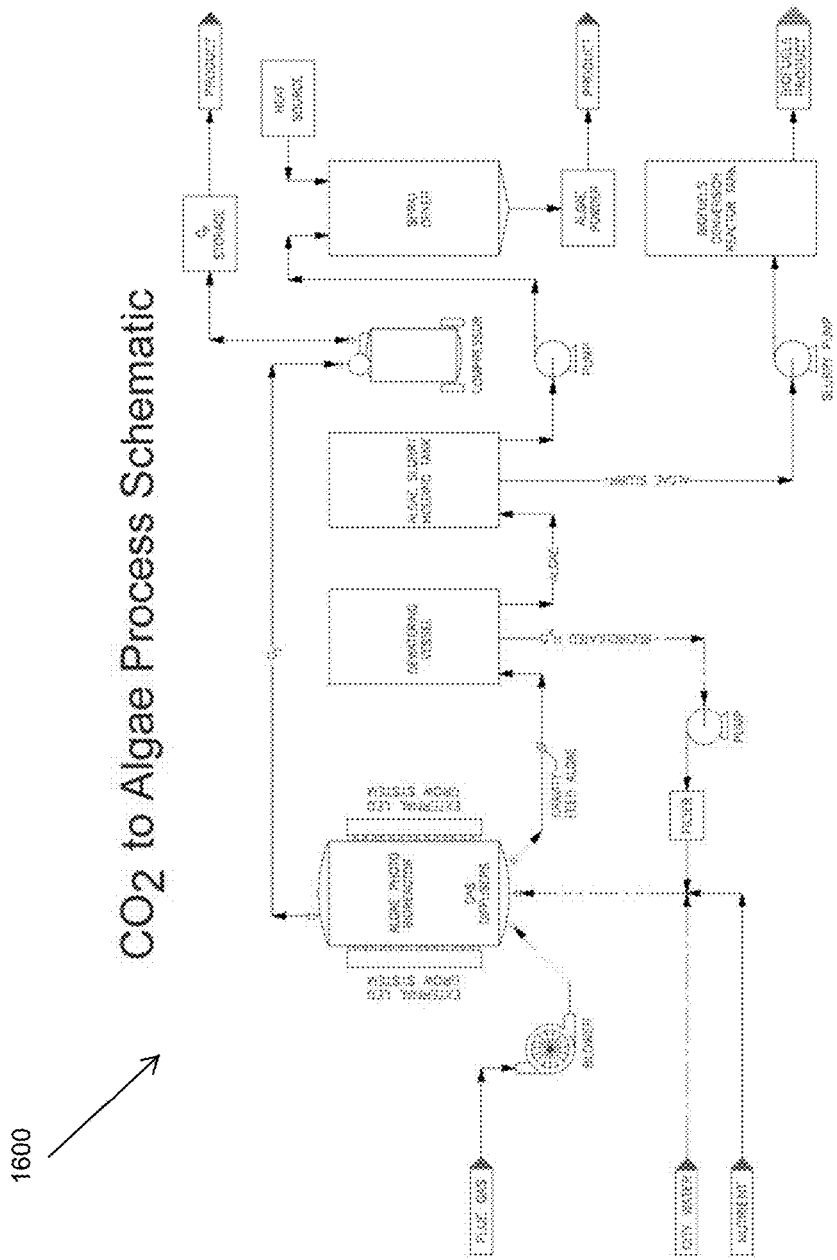
FIG. 16 is a schematic diagram of a system to reduce carbon dioxide in emissions using an algae process.
Figure 17:
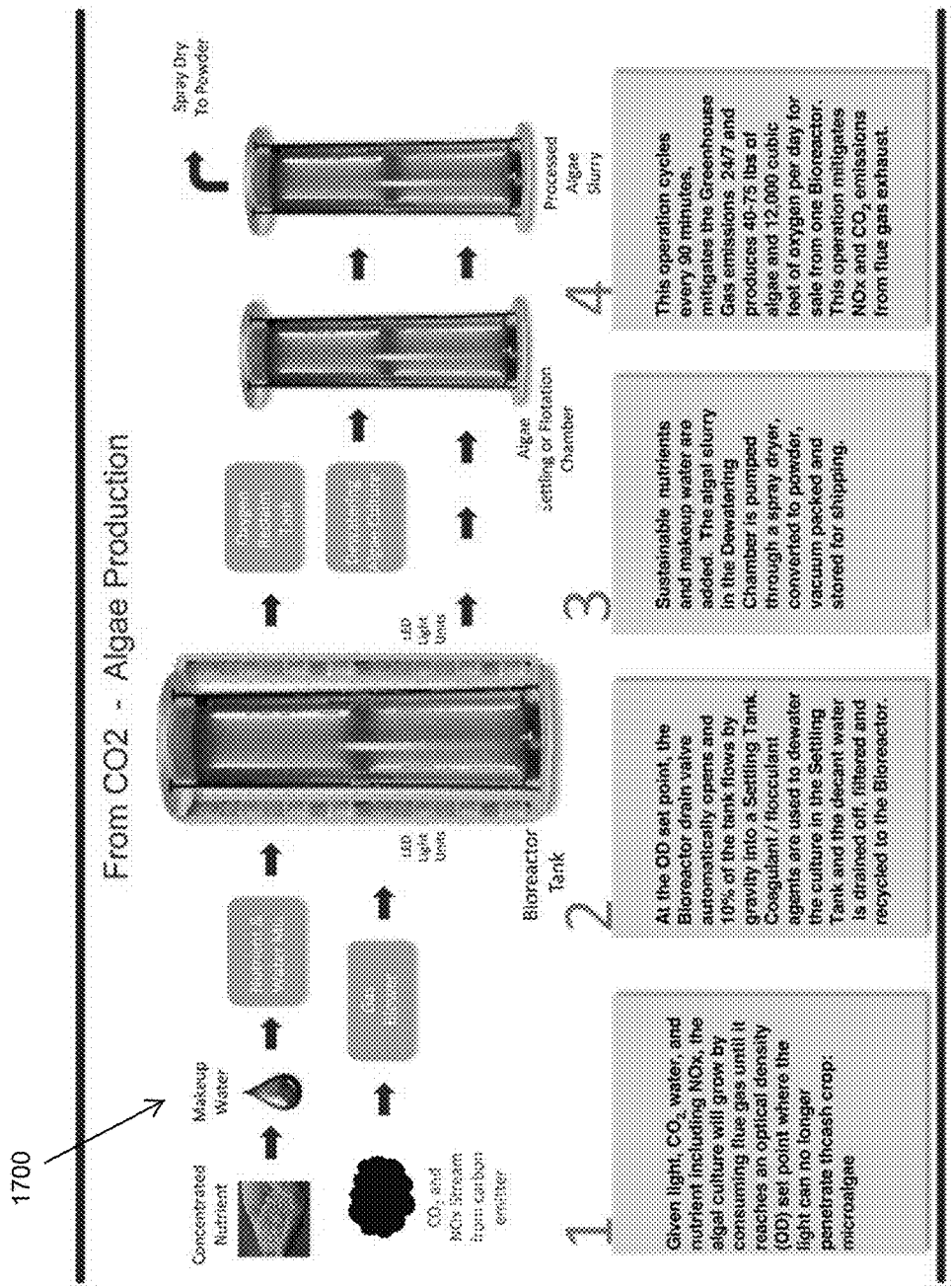
FIG. 17 illustrates how the algae process of FIG. 16 works to reduce carbon dioxide in emissions.

FIG. 16 is a schematic diagram 1600 of one example of a system to reduce carbon dioxide in emissions using an algae process. FIG. 17 illustrates how the algae process of FIG. 16 works to reduce carbon dioxide in emissions. The process 1700 involves four basic steps, as illustrated in both FIGS. 16 and 17. Given light, $CO_2$, water and nutrients, including, $NO_x$, the algal culture will grow by consuming flue gas until it reaches an optical density (OD) set point where the light can no longer penetrate the cash crop microalgae. In step two, at the OD set point, the bioreactor drain valve automatically opens and 10% of the tank flows by gravity into a setting tank. Coagulant/flocculent agents are used to dewater the culture in the settling tank and the decant water is drained off, filtered and recycled to the bioreactor. At set three, sustainable nutrients and makeup water are added. The algal slurry in the dewatering chamber is pumped through a spray dryer, converted to powder, vacuum packed and stored for shipping. This operation cycles every 90 minutes, mitigates the greenhouse gas emissions 24/7 and produces 40-75 lbs of algae and 12,000 cubic feet of oxygen per day for sale from one bioreactor. This operation mitigates $CO_2$ and $NO_x$ emissions from flue gas exhaust.

A method for treating exhaust from auxiliary diesel engines operated by ocean-going ships at-berth is also provided by the present invention. The method includes the step of providing a movable exhaust treatment system that may be located alongside the ship that can remain in continuous operation while the ship's engines are running. The method comprises the steps of incorporating an emissions control system 104 within a housing 120, connecting the emission control system 104 to the stack 103 of the diesel engine 105 of the ship 107 by an emissions capture system 102 that allows the exhaust from the diesel engine to be passed through the emissions control system 104 and emit regulatory compliant air from the exhaust outlet 103 of the ship 107 when the ship 107 is at berth.

While the above descriptions are described in operation with the auxiliary engines of the ship, the system may be used with any of the ships engines. The foregoing description of an implementation of the invention has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A method for allowing ships having diesel engines and exhaust outlets to achieve emission reductions at-berth, the method comprising the steps of:
   (a) incorporating an emissions control system within a housing, the emissions control system having an exhaust inlet for receiving diesel engine exhaust and an exhaust outlet; and
   (b) connecting the emissions control system to the ship's diesel engine exhaust by a telescopic duct, where the telescopic duct connects directly to the exhaust inlet of the emissions control system and captures and transports the ship's diesel exhaust to the emissions control system, where the exhaust is passed through the emissions control system to emit regulatory compliant air from the exhaust outlet of the emissions control system.

2. The method of claim 1, where the emissions control system continuously operates while connected to the ship's diesel engine when the ship is at-berth.

3. A method for reducing emissions from a ship's exhaust, the method comprising the steps of:
   (a) providing an emissions capturing system for capturing the ship's exhaust from the ship's exhaust stack for treatment, the emissions capturing system including a telescopic duct mounted on a telescopic crane where the telescopic crane is capable of extending or retracting the telescopic duct over the ship's exhaust stack to capture the exhaust emitted from the exhaust stack; and
   (b) connecting the emissions capturing system to an emissions control system positioned within a housing, the emissions control system having a filter housing for cleaning air by removing certain levels of pollutants in the ship's exhaust.

\* \* \* \* \*